United States Patent [19]

Spence

[11] Patent Number: 4,706,839
[45] Date of Patent: Nov. 17, 1987

[54] CLOSURES AND METHODS OF CLOSURE FOR A STERILIZATION CONTAINER SYSTEM

[75] Inventor: Jerry L. Spence, Kirkland, Wash.
[73] Assignee: Instrumed, Inc., Kirkland, Wash.
[21] Appl. No.: 925,412
[22] Filed: Oct. 31, 1986
[51] Int. Cl.[4] ...................... B65B 53/00; B65B 31/00; B65D 81/18
[52] U.S. Cl. ...................................... 220/315; 53/399; 53/421; 53/425; 206/438; 206/497; 206/605; 220/357; 422/300
[58] Field of Search .................. 53/111 R, 139.3, 399, 53/410, 412, 416, 420–422, 424, 425, 428, 440–442, 449, 485, 487, 556, 557, 582; 206/438, 497, 605, 610; 220/214, 256, 257, 315, 319, 320, 400, 357; 229/DIG. 12; 422/25, 26, 38, 291, 307, 300

[56] References Cited

U.S. PATENT DOCUMENTS

| | | | |
|---|---|---|---|
| 3,528,825 | 9/1970 | Doughty | 206/497 |
| 3,733,002 | 5/1973 | Fujio | 229/DIG. 12 |
| 3,820,205 | 6/1974 | Shaw | 53/442 |
| 3,826,059 | 7/1974 | Novitch | 53/412 |
| 4,015,401 | 4/1977 | St. Amand et al. | 53/425 |

FOREIGN PATENT DOCUMENTS 2289394  5/1976  France ................................. 53/442

OTHER PUBLICATIONS

"Shrinkable Packaging Materials," Jerry L. Spence, Dec. 1986.

Primary Examiner—Jimmy G. Foster
Attorney, Agent, or Firm—Gregory W. Moravan

[57] ABSTRACT

Closures for a sterilization container system comprising at least one band of shrinkable material encircling the base and lid of a sterilization container system. The closures are formed from a shrinkable material which, when exposed to a shrinking agent, shrinks to pull said lid and base tightly against each other for the goal of providing a microorganism proof seal to prevent the entry of microorganisms into the interior of the sterilization container system. Also disclosed are the method of using the closures to achieve that goal, and the method of using at least one agent which simultaneously shrinks the at least one band of shrinkable material and sterilizes the sterilization container system and its contents.

8 Claims, 1 Drawing Figure

CLOSURES AND METHODS OF CLOSURE FOR A STERILIZATION CONTAINER SYSTEM

BACKGROUND OF THE INVENTION

The present invention relates to closures for sterilization container systems. More particularly, it relates to new and innovative closures and methods of closure for the same which involve no mechanical latching devices at all.

SUMMARY OF THE INVENTION

A sterilization container system is a reusable device used to hold materials, such as surgical instruments, while they are being sterilized, and to keep them sterile until they are ready to be used. A typical sterilization container system is a container comprising a base; a removable lid; a gasket for providing a microorganism proof seal between the base and lid; and filter means which are arranged to permit the entry of the sterilant (such as steam or ethylene oxide) into the container, but which do not permit the entry of microorganisms. The gasket is typically affixed to the lid or the base, as by a compression fit.

Since, as mentioned, one of the primary functions of a sterilization container system is to keep it sterilized contents sterile until they are needed, it is apparent that the base, lid and gasket must be held tightly together so they do, in fact, form the desired microorganism proof seal therebetween.

Conventional closures for the base and lid of a sterilization container system are typically mechanical latching devices. Such mechanical latches suffer from numerous drawbacks. Among them are that they are relatively complex and thus they are costly to manufacture, assemble and install. They are also costly to manufacture because they are likely to be made from expensive stainless steel, since stainless steel is not adversely affected by the sterilant. In fact, the manufacture, assembly and installation of the stainless steel latch and handle assembly on a sterilization container system currently on the market comprises about 40% of the total cost of making the sterilization container system.

In addition, being what they are—mechanical devices—mechanical latches are inherently subject to mechanical wear, damage, breakage and failure.

Further, mechanical latches are typically installed on the base and lid of the sterilization container system by the use of rivets. Unfortunately, since rivets require rivet holes, it is apparent that either by improper installation or wear over time, such rivet holes may leak and permit the insidious, undetected entry of microorganisms into the sterilization container system, thereby contaminating the contents and possibly resulting in the illness or even the death of the patent upon whom the supposedly sterile contents were used. And even if the rivet holes didn't leak, the wear, damage, breakage or failure of the mechanical latches could result in a poor seal betweeen the base, lid and gasket, thereby leading to the undetected entry of microorganisms into the sterilization container system with harmful and even fatal consequences for the patient upon whom the supposedly sterile contents were used.

Further, such mechanical latches are typically provided with safety seals to provide an indication as to whether or not they have been opened, since if they are inadvertently opened prematurely the contents of the sterilization container system must be presumed to be contaminated, to be on the safe side. Such safety seals are additional expense items which are inconvenient to install and which take costly time to install. And if they are not installed because of an oversight, the result is that the sterilization container system must be presumed to have been opened and thus contaminated, necessitating the costly resterilization of the sterilization container system and its contents.

Despite all of the above disadvantages inherent with mechanical latches for sterilization container systems, to the inventor's W knowledge they are the only means presently in use in the industry to seal the base, lid the gasket of sterilization container systems together.

The present invention is intended to avoid all of the above problems since it completely eliminates the need for conventional mechanical latches to seal together the base, lid and gasket of a sterilization container system.

Instead of a conventional mechanical latch, the present invention employs at least one, and preferably two or more loops of conventional heat shrink polyvinyl chloride (PVC) which pass completely around the sterilization container system. Then, when the sterilization container system is exposed to heat within a heat or steam based sterilizing device, the PVC loop(s) shrink, thereby automatically pulling the base, lid and gasket into a tight microorganism proof seal. In addition, the PVC loops automatically form a safety seal since by their very presence when unbroken, they indicate the sterilized sterilization container system has not been opened or compromised.

By way of cost comparison, a pair of PVC loops costs much less than one percent of the cost of the sterilization container system, as compared to the mechanical latch and handle assembly of a conventional sterilization container system being about 40% of the total cost of making the sterilization container system.

If a cold sterilizing process is used, then prior to the sterilizing of the sterilization container system and its contents, the installed heat shrink loops may be shrunk with any convenient heat source, such as a hair dryer.

The foregoing is intended to be but a brief summary of, not a detailed catalog of, the objects, features, advantages and characteristics of the present invention, since there and further objects, features, advantages and characteristics of the present invention will be either expressly or inerently disclosed to those of ordinary skill in the art in view of the disclosures herein.

DESCRIPTION OF THE PREFERRED EMBODIMENTS

Figure 1:
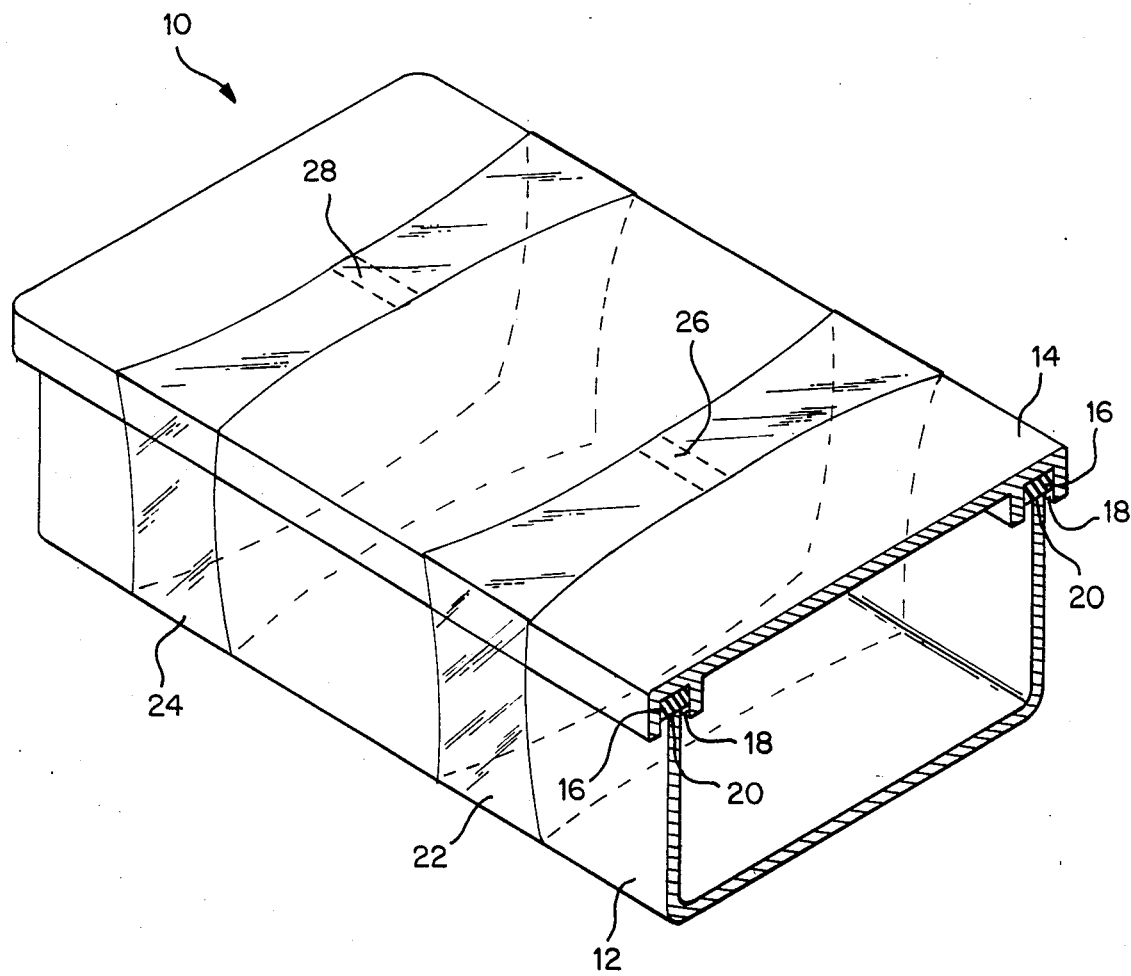
FIG. 1 is a perspective view of the present invention in operation, with one end of the sterilization container system being shown in cross section to permit viewing of some of its details of construction.

Turning now to FIG. 1, it diagrammatically illustrates a typical conventional sterilization container system 10. Sterilization container system 10 is simply a box or container having a base 12, a removable lid 14 and a gasket 16 mounted in a gasket channel 18 in lid 14. Gasket 16 and its channel 18 extend completely around the periphery of lid 14; and the upper edge 20 of base 12 extends completely around the periphery of base 12. The cut away end of sterilization container system 10 is identical to the other end of sterilization container system 10, and is not illustrated for clarity. Gasket 16 and gasket channel 18 might be eliminated if the top 20 of base 12 was designed to seal directly against a smooth undersurface of lid 14. Other features of sterilization container system 10 are not illustrated because they are all conventional and well known in the art; because they bear no relationship to the operation of the present invention; and because sterilization container system 10 forms no part, per se, of the present invention.

When lid 14 is assembled to base 12, the upper edge 20 of base 12 contacts the lower surface of gasket 16. In order to provide a tight, microorganism proof seal between base 12, lid 14 and gasket 16, a pair of bands 22, 24 are provided.

Bands 22, 24 are preferably composed of any conventional material which shrinks under the influence of heat, such as, by way of non-limiting example, heat shrink polyvinyl chloride (PVC). But it is within the scope of the present invention that bands 22, 24 could be composed of a variety of substances which shrink under the influence of some other shrink inducing agent besides heat such as, by way of non-limiting example, radiation, visible and invisible electromagnetic radiation, chemical(s) or drying. Bands 22, 24 are shown as being transparent, but could be translucent or opaque.

By way of non-limiting example, if sterilization container system 10 were about two feet long, about one foot wide, and about five inches thick, bands 22, 24 could be about 4 inches wide, and about 3.5 mils thick.

Prior to being shrunk, bands 22, 24 are sized to be only slightly larger in circumference than the circumference of an assembled sterilization container system 10, so that when bands 22, 24 are shrunk, as much of their shrinkage as is possible will go towards pulling base 12, lid 14 and gasket 16 into a tight, microorganism proof seal, rather than going towards taking up excess slack in bands 22, 24.

The width, thickness, number and material of bands 22, 24 are selected such that when bands 22, 24 are shrunk, they urge base 12, lid 14 and gasket 16 tightly against each other in a tight, microorganism proof seal. But they are not shrunk to the point where they break or might tend to break under the forces expected to be encountered during the normal handling, sterilization and storage of sterilization container system 10. Instead, their width, thickness, number and material should be selected with a substantial safety factor in mind.

Band(s) 22 or 24 are preferably located on sterilization container system 10 so as to uniformly distribute the loading they exert on sterilization container system 10 to better ensure a secure, tight, microorganism proof seal between all sealing portions of base 12, lid 14 and gasket 16; and are preferably located so as to not interfere with any filter openings provided in sterilization container system 10 for the entry and/or exit of the sterilant.

In use, bands 22, 24 are slipped over and located in their desired location on sterilization container system 10. Then sterilization container system 10, with its bands 22, 24 are inserted into the sterilization device, such as a sterilization device which utilizes steam as the sterilant. Then the same heat and temperature which is utilized to sterilize sterilization container system 10 and its contents will automatically act as the agent which causes the heat shrink PVC bands 22, 24 to shrink to the desired degree so they urge base 12, lid 14 and gasket 16 into the desired tight microorganism proof seal.

In a typical conventional steam sterilization process, steam at a temperature of 270° F. is used for at least several minutes to sterilize the sterilization container system and its contents. At that temperature the PVC bands shrink to the desired tightness in only about 10 seconds so at the end of the sterilization cycle, the sterilization container system has long since been sealed by the shrunk PVC loops.

In general, it is preferred that the sterilant (whatever it might be) which is used to sterilize sterilization container system 10 and its contents also be used as the shrinkage inducing agent which is used to shrink bands 22, 24. This is highly desirable for economy, efficiency and increased ease of operation since both the sterilizing and the shrinking are then done in one step.

Alternatively, the heat or other shrinkage inducing agent could, of course, be applied to bands 22, 24 before sterilization container system 10 was inserted into a sterilizing device.

When it is desired to open the sealed sterilization container system 10, the perforated or other tear strips 26, 28 on bands 22, 24 are torn, thereby releasing bands 22, 24. Alternatively, tear strips 26, 28 could be eliminated and bands 22, 24 could be cut, as with a knife or scissors.

In view of the disclosures herein, various further adaptations, modifications, and uses of the present invention will now be apparent to those in the art to which it pertains, within the scope of the claims appended hereto; it being understood that all of the descriptions and illustrations contained herein regarding the present invention are strictly by way of non-limiting example.

What is claimed is:

1. A method of closure for a sterilization container system comprising a base, a lid, and a gasket means adapted to provide a selectively releasable seal with at least one of said lid and said base; wherein said method comprises the steps of:
    a. encircling said base and said lid with at least one band of shrinkable material;
    b. placing said sterilization container system bearing said at least one band of shrinkable material into a device for sterilizing said sterilization container system and its contents; and
    c. exposing said sterilization container system bearing said at least one band of shrinkable material to at least one sterilant within said device for sterilizing until said sterilization container system is sterilized and until said at least one band of shrinkable material shrinks to the point where it urges said base, lid and gasket firmly together to provide a selectively releasable microorganism proof seal between at least two of said base, lid and gasket means to prevent microorganisms from entering an interior space of said sterilization container system; and wherein said at least one sterilant within said device for sterilizing acts to sterilize said sterilization container system and its said contents and acts to simultaneously shrink said at least one band of shrinkable material.

2. The method according to claim 1, wherein step a. further comprises: encircling said base and said lid with said at least one band of shrinkable material in a direction such that said at least one band of shrinkable material extends transversely across a line of intersection between said base and said lid.

3. A method of closure for a sterilization container system comprising a base, a lid and a gasket means adapted to provide a selectively releasable seal with at least one of said lid and said base; wherein said method comprises the steps of:
  a. encircling said base and said lid with at least one band of shrinkable material; and
  b. exposing said at least one band of shrinkable material to a shrink inducing agent until said at least one band of shrinkable material shrinks to the point where it urges said base, lid and gasket means firmly together to provide a selectively releasable microorganism proof seal between at least two of said base, lid and gasket means to prevent microorganisms from entering an interior space of said sterilization container system.

4. The method according to claim 3, wherein step a. further comprises: encircling said base and said lid with said at least one band of shrinkable material in a direction such that said at least one band of shrinkable material extends transversely across a line of intersection between said base and said lid.

5. A closure means in combination with a sterilization container system comprising a base, a lid, and a gasket means adapted to provide a selectively releasable seal with at least one of said lid and said base; wherein said closure means comprises at least one band of shrinkable material encircling said base and said lid; said at least one band being shrunk to such a degree that it urges said base, lid and gasket means firmly together providing a selectively releasable microorganism proof seal between at least two of said base, lid and gasket means to prevent microorganisms from entering an interior space of said sterilization container system.

6. A closure means for a sterilization container system according to claim 5, wherein said at least one band of shrinkable material includes a tear strip means for selectively breaking said at least one band of shrinkable material when desired.

7. The closure means according to claim 6, wherein said at least one band of shrinkable material encircles said base and said lid in a direction such that said at least one band of shrinkable material extends transversely across a line of intersection between said base and said lid.

8. The closure means according to claim 5, wherein said at least one band of shrinkable material encircles said base and said lid in a direction such that said at least one band of shrinkable material extends transversely across a line of intersection between said base and said lid.

* * * * *